United States Patent [19]

Herold et al.

[11] 4,412,134
[45] Oct. 25, 1983

[54] APPARATUS FOR IRRADIATING DENTAL OBJECTS

[75] Inventors: Wolf-Dietrich Herold, Hechendorf; Karl L. Grafwallner, Munich; Michael Keller, Lochham, all of Fed. Rep. of Germany

[73] Assignee: ESPE Fabrik Pharmazeutischer Praeparate GmbH, Seefeld, Fed. Rep. of Germany

[21] Appl. No.: 283,690

[22] Filed: Jul. 15, 1981

[51] Int. Cl.³ .......................... C08F 2/48; C08G 2/02; C08U 7/10

[52] U.S. Cl. .......................... 250/504 R; 250/455.1; 250/494.1

[58] Field of Search ............... 250/455.1, 494.1, 504

[56] References Cited

U.S. PATENT DOCUMENTS

| | | | |
|---|---|---|---|
| 2,245,762 | 6/1941 | Stefani et al. | 250/455.1 |
| 2,822,476 | 2/1958 | Osgood | 250/455.1 |
| 4,149,086 | 4/1979 | Nath | 250/504 |
| 4,157,253 | 6/1979 | Hernquist | 250/504 |
| 4,241,255 | 12/1980 | Sugiyama et al. | 250/504 R |

Primary Examiner—Alfred E. Smith
Assistant Examiner—Jack I. Berman
Attorney, Agent, or Firm—Holman & Stern

[57] ABSTRACT

An apparatus for treating, particularly bleaching, dental objects, such as dentures or parts thereof, made of synthetic material includes a support disposed in a drawer for receiving the objects and a lamp disposed above the drawer for emitting radiation in a spectral range (approximately 400 to 500 nm) suitable for the bleaching process. An upper reflector surrounding the lamp reflects from the total radiation emitted by the lamp mainly the portion lying within the said spectral range while it transmits the remaining radiation to the outside. An inner surface of the drawer forms a lower reflector. The support also consists of reflective material and has a central semi-spherical projection to ensure that the object positioned on the support so as to surround the projection is irradiated from all sides.

In another embodiment, the support for the dental object is made of glass, and two lamps each surrounded by a reflector are used to irradiate the object from above and below. In this case, the upper lamp and reflector are disposed to emit light in a substantially horizontal direction, and a mirror is disposed above the support to redirect the irradiation towards the object. The mirror is mounted on a lid which is removable to allow easy access to the support.

The support may be disposed in a vacuum-tight chamber connected to a vacuum pump.

10 Claims, 7 Drawing Figures

APPARATUS FOR IRRADIATING DENTAL OBJECTS

BACKGROUND OF THE INVENTION

In the dental practice, certain synthetic compositions are used for making artificial dental parts, such as crowns, individual teeth, bridges, dentures or parts thereof, which compositions exhibit an undesired tinge of yellow caused by the specific color of polymerisation initiators contained therein. Such tinge may be permanently removed in a subsequent bleaching step by an irreversible reaction actuated by radiation to obtain a hue corresponding to the natural tooth color. Typically, radiation in a range from about 400 nm to about 500 nm (with a maximum at about 460 nm) is required for this bleaching process, the irradiation taking place over a substantial period of time of for instance 30 min. This irradiation at the same time results in a desired post-polymerisation of the material.

German Offenlegungsschrift No. 29 01 534 discloses an irradiation apparatus for use in the dental field which employs radiation in the UVA spectral range (about 320 nm to about 400 nm) or in the near-UVA visible spectral range, for curing dental fillings made of synthetic material. In order to direct the radiation to the limited area of a tooth filling within the mouth of a patient, the desired spectral portion of the radiation emitted by a lamp is focussed by an ellipsoidal selective reflector onto the input end of an optical wave guide and directed by means of the wave guide onto the location to be irradiated over a period of time of for instance 20 to 30 s. During this relatively short irradiation period, the known apparatus is hand-held by the dentist. The selective reflector of the known apparatus ensures that only the desired radiation enters the optical waveguide while both, dangerous radiation of shorter wavelengths and heat radiation predominantly produced by the lamp, are transmitted through the reflector to the rear side thereof.

The known apparatus is not suited for the present purpose of a bleaching treatment, because it is designed as a hand-held device, because it is made for irradiating very limited areas only, and because of the shortness of the individual periods of operation.

It is an object of the invention to provide an apparatus for irradiating dental objects which permits a uniform irradiation of substantially the entire surface of the objects during a comparatively long period of time and which exploits the desired radiation produced as completely as possible.

Another object of the invention is to provide an apparatus of the above type, which is simple in operation and easy to handle.

As a further object of the invention, an apparatus should be provided which irradiates all free surfaces of the respective object without requiring a rotation or other movement of the object during the irradiation procedure.

It is another object of the invention to devise an apparatus for irradiating dental objects with radiation of a desired "cold" spectral range, at the same time avoiding any heating of the object as completely as possible. This is of particular importance because excessive temperatures may damage or destroy the synthetic material of the objects. Furthermore, in dental objects containing parts of metal and parts of synthetic material, excessive heat may deteriorate the connection between the different parts due to the difference in their thermal expansion coefficients. In view of this particular problem, it is another object of the invention to devise an apparatus for irradiating dental objects so that the temperature of the object is maintained below about 50° C.

As a further object of the invention, an apparatus for irradiating dental objects is to be provided, which allows an evacuation of the treatment zone. Such evacuation may be required if the respective dental object to the irriadiated is made of a polymer which tends to form undesired layers on its surface when exposed to oxygen during the irradiation process.

It is a further object of the invention to provide an apparatus for irradiating dental objects, which apparatus allows easy access to the treatment zone for inserting and removing the respective dental objects, as well as to the lamp or lamps which form the only parts that require replacement from time to time.

It is a further object of the invention to provide for an automatic switching-off of the irradiation apparatus upon expiry of a settable period of time and to avoid both, excessive and insufficient irradiation periods.

The above and further objects are met by an apparatus for treating dental objects with radiation of a selected spectral range as defined in the appending patent claims.

DETAILED DESCRIPTION OF THE PREFERRED EMBODIMENTS

Figure 1:
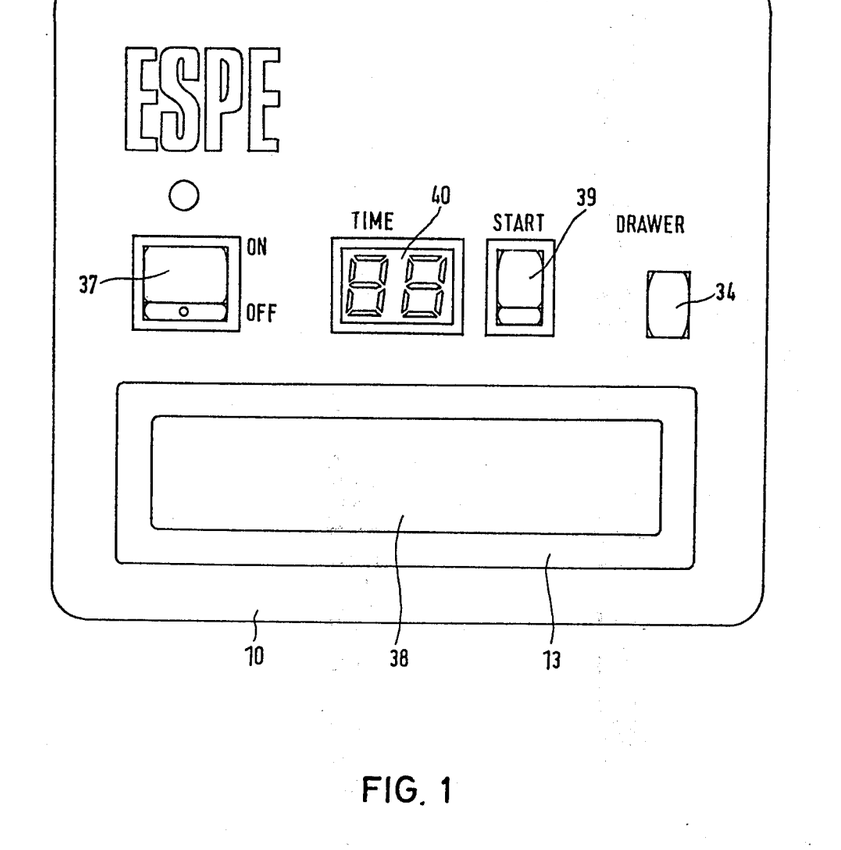
FIG. 1 shows a front view of an irradiation apparatus according to a first embodiment of the invention.
Figure 2:
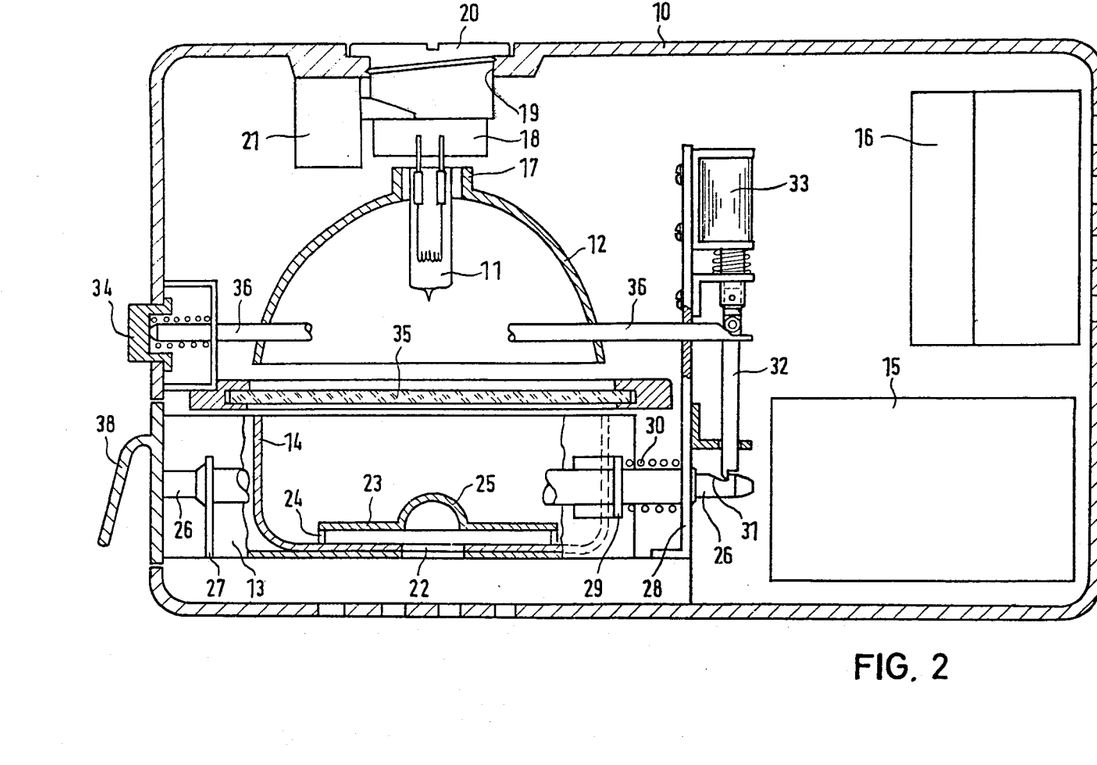
FIG. 2 is a schematic vertical cross section of the apparatus shown in FIG. 1.
Figure 3:
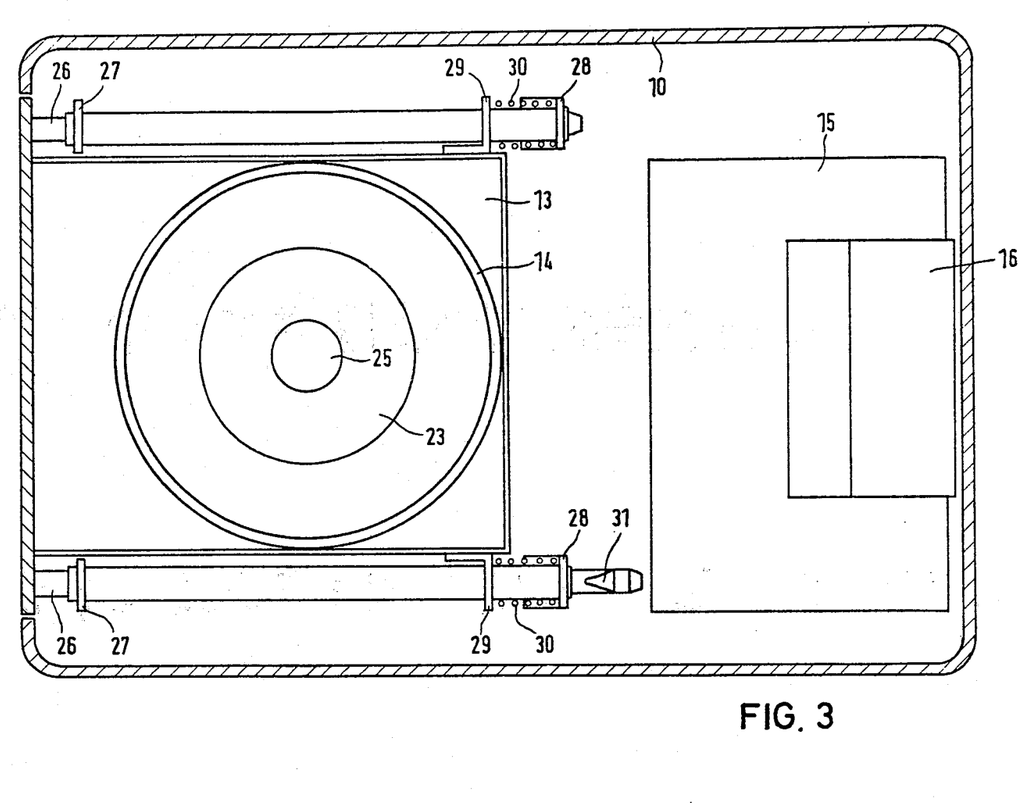
FIG. 3 is a schematic horizontal cross section through the apparatus of FIG. 1.

In the embodiment of FIGS. 1 to 3, the irradiation apparatus includes a housing 10, in which a lamp 11 with a first reflector 12, a second reflector 14 located in a drawer 13, an electrical control circuit 15 and a blower 16 are disposed. The reflector 12 is in the shape of a paraboloid and has a central flange 17 with an opening through which the lamp 11 extends. The lamp 11 is preferably a halogen-tungsten low-voltage lamp as is otherwise used in movie and slide projectors. The lamp is inserted in a socket 18 disposed above the flange 17, the socket being accessible through an opening 19 provided in the upper wall of the housing 10. The opening 19 is closed by a screw 20. For exchanging the lamp 11, the screw 20 is opened and the socket 18 including the lamp is withdrawn upwardly through the opening 19 of the housing. A switch 21 ensures that the current supply to the lamp 11 is interrupted whenever the socket 18 is not in its predetermined position.

The drawer 13 is shown in FIGS. 1 to 3 in its fully inserted position. According to FIGS. 2 and 3, the pot-shaped second reflector 14 is placed in the drawer 13, and its upper circular opening has the same size as the downwardly facing opening of the paraboloidal first reflector 12, the openings of the two reflectors being aligned with each other in the completely inserted position of the drawer 13. The second reflector 14 has a ventilation opening 22 in its lower portion. The opening 22 is covered by a table 23 which serves to support the dental objects to be irradiated and which is spaced by legs 24 from the lower surface of the reflector 14. The table 23 consists of highly reflective material and has a central convex, semispherical projection 25. This structure of the table 23 permits air to pass through the opening 22 while at the same time preventing radiation from leaking through the opening 22.

As shown in FIGS. 2 and 3, the drawer 13 is provided with lateral guide rods 26 which pass through bores provided in stop members 27 disposed close to the front side of the housing, the rear free ends of the end guide rods 26 extending through further bores provided in guide members 28, when the drawer is completely closed. Helical springs 30 are located between the guide members 28 fixed to the housing and stop members 29 mounted on the drawer 13 to bias the drawer in the direction of its opening movement. In connection with the stop members 27 fixed to the housing, the stop members 29 mounted on the drawer 13 have the further purpose of limiting the opening movement of the drawer.

One of the two guide rods 26 is provided at its free rear end with a notch 31 which, in the completely inserted position of the drawer 13, is engaged by the end of a locking rod 32. As will be understood from FIG. 2, the locking rod 32 may be withdrawn either by actuating an electromagnet 33 or by means of a rod 36 actuated by a pressure button 34 located in the front wall of the housing (FIG. 1), in such a manner that it is disengaged from the notch 31, thereby releasing the drawer 13 to open under the action of the spring 30.

The upper reflector 12 surrounding the lamp 11 is preferably formed as a selective reflector which reflects from the total radiation emitted by the lamp 11 only the spectral portion lying in the desired spectral range (approximately 400 to 500 nm) while transmitting or passing, without absorption, the portion of the radiation lying outside this desired spectral range. A reflector of this type consists for instance of a quartz glass substrate body with a thin-film filter reflective in the desired spectral range being coated by evaporation on the inner surface of the substrate. This selective reflector is particularly advantageous in that a large portion of the radiation emitted by the tungsten-halogen lamp used lies above 500 nm and represents predominantly undesired heat radiation.

Due to the paraboloidal shape of the reflector 12, the desired radiation of the lamp 11 is reflected vertically downwardly. The lower reflector 14 in this case is made of aluminum and may have a roughened surface to reflect the incident radiation in a diffuse manner. The desired radiation emitted by the lamp 11 is thus reflected forth and back in various directions between the two reflectors 12 and 14 so that practically the entire desired radiation will reach the irradiation object disposed on the table 23. The central reflecting projection 25 of the table 23 ensures an irradiation of the inner surface of larger denture portions.

An absorption filter 35 which transmits only the desired radiation and absorbs the other spectral ranges, may be disposed at the lower opening of the upper reflector 12. Such an absorption filter will be provided particularly in case the upper reflector 12 is not formed as a selective reflector as described above but reflects all radiation emitted by the lamp 11. Instead of, or in addition to, the absorption filter 35, the lower reflector 14 may be formed as a selective reflector.

The blower 16 located within the housing 10 serves to remove the heat passing through the reflectors 12 and 14, thereby cooling these reflectors, and to produce an air current through the spacing between the two reflectors, the interior space of the lower reflector 14 containing the irradiation objet and through the lower opening 22 of the lower reflector 14. This air circulation, the use of at least one selective reflector and the possible use of an absorption filter effectively avoid an undesired heating of the irradiation object. Since the absorption filter 35 is disposed in the spacing between the two reflectors, which spacing is exposed to the air current, the filter itself is well cooled. The blower 16 has the further task of cooling the socket of the lamp 11. This cooling is of significance because the suspended installation of the lamp 11 as shown in FIG. 2 might otherwise result in an unallowable heating of the lamp socket which may damage the lamp. An air current produced by the blower 16 flows through the spacing provided between the upper side of the filter 35 and the lower rim of the reflector 12 into the interior of the reflector 12 and past the lamp 11 and escapes through the air gap existing between the upper rim of the flange 17 and the lower side of the socket 18.

When the absorption filter 35 is not provided, the air current produced by the blower 16 may directly flow from the lower ventilation opening 22 through the interior of the two reflectors 12 and 14 past the lamp 11 and escape through the gap between the flange 17 and the socket 18.

In operation of the apparatus, a mains switch 37 disposed on the front plate (FIG. 1) of the housing is switched on. By pressing the button 34, the drawer 13 will then be opened and withdrawn by means of a handle 38. The dental object to be treated is placed onto the table 23 located in the lower reflector 14, and the drawer is closed. Actuating a start switch 39 also provided on the front plate of the housing will switch on the lamp 11. Simultaneously, a counter 70 provided in the control circuit 15 is initiated to control a digital display 40 provided again on the front plate of the housing. Upon expiry of the predetermined period of time, as determined by timer 71, the control circuit 15 will switch off the current supply of the lamp 11 and simultaneously actuate the electromagnet 33 which will raise the locking rod 32 thereby releasing the drawer and causing it to open under the action of the spring 30. The finished dental object may then be removed.

In case the lamp 11 should fall during a treatment cycle, the control circuit 15 will sense the interruption of the current flowing through the filament of the lamp by means of sensor 72 and stop the counter, thereby also stopping the digital display 40. In this case, the drawer 13 will remain closed. To provide the operator with a signal indicating the failure of the lamp, the digital display is actuated with current pulses via pulser 73 to produce a flashing signal. In addition or alternatively, an audible signal may be produced. The operator will then exchange the lamp and thereafter switch on the lamp and continue the cycle by reactuating the start switch 39. This prevents an uncontrolled insufficient irradiation of the object in case of failure of the lamp.

Furthermore, in order to avoid a premature removal of the irradiation object, a modification of the apparatus provides that the pressure button 34 acts on a switch disposed in the supply circuit of the electromagnet 33 rather than directly on the locking rod 32, which switch is rendered inoperative during a running cycle by the control circuit 15.

Figure 4:
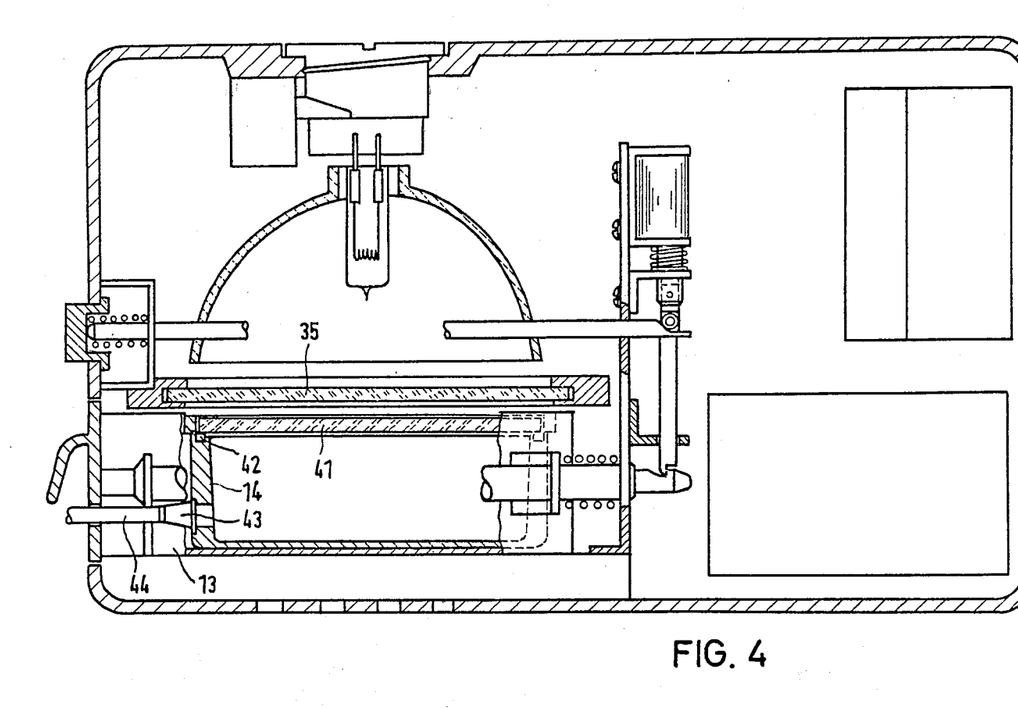
FIGS. 4 and 5 show two modifications of the apparatus in representations similar to that of FIG. 2.
Figure 5:
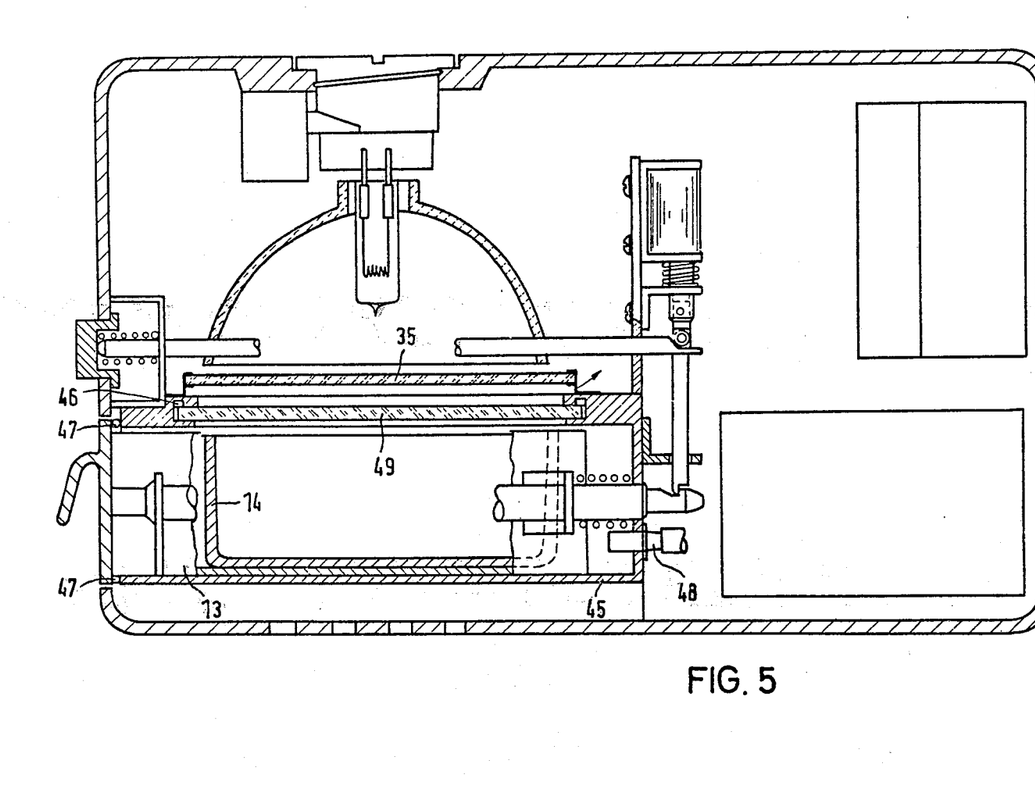

In the modifications of the irradiation apparatus shown in FIGS. 4 and 5, means for evacuating the treatment zone are provided. Such an evacuation is required for instance when the irradiation object consists of a polymer on which a smeary layer forms during the irradiation procedure by an interaction with oxygen.

In the embodiment of FIG. 4, the reflector 14 disposed within the drawer 13 is sealed in a vacuum-tight manner by an upper glass plate 41 and a sealing 42. The glass plate 41 is highly permeable for the radiation used, i.e. in a range centered at approximately 460 nm. Suitable for this purpose are particularly quartz glasses having a high permeability and preferably also a high heat resistance. The reflector 14 has in its front wall an opening with a fitting 43 connected to a vacuum pump 74 (shown schematically in FIG. 7) via hose 44 extending through the front plate of the drawer 13. For emptying the drawer upon the irradiation treatment, the vacuum pump is switched off and the drawer is vented so that the glass plate may be easily lifted. The switching-off of the vacuum pump is preferably done automatically by the control circuit 15.

In the embodiment of FIG. 5, the drawer 13 is located in a housing portion 45 which is closed at all sides, except a front opening, and which is sealed in a vacuum-tight manner by an upper glass plate 49 and a sealing 46. Just as the glass plate 41 in the embodiment of FIG. 4, the glass 49 has a high permeability for radiation and also a high thermal resistance. The front opening of the housing portion 45 is provided with a sealing 47 which is abutted by the front plate of the drawer 13 in the closed condition of the drawer. A vacuum terminal 48 is mounted in the rear wall of the housing portion 45 and connected to a vacuum pump 74 which in this case may be located inside the housing 10. Just as in FIG. 4, the filter 35 (also provided in the embodiment of FIG. 2) is disposed above the glass plate 49 in such a manner that it is exposed on all sides to cooling air.

The embodiment of FIG. 5 is advantageous over that of FIG. 4 in that the vacuum connection is made at a stationary housing portion, thus does not impede the movement of the drawer.

Although not shown in FIGS. 4 and 5, a table 23 for supporting the irradiation object is disposed in the middle of the drawer 13, as explained in connection with FIG. 2. In contrast to FIG. 2, however, the drawer 13 in the embodiments of FIGS. 4 and 5 is not provided with a ventilation opening 22 but closed.

Figure 6:
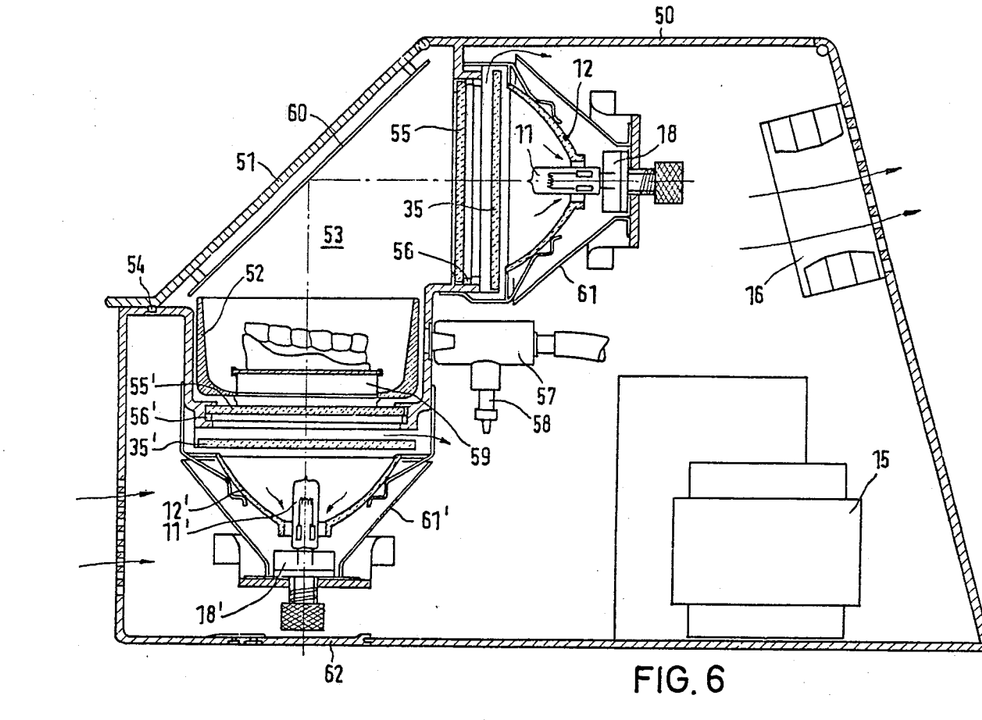
FIG. 6 is a vertical cross section through an irradiation apparatus in a second embodiment of this invention.

In the embodiment shown in FIG. 6, the irradiation apparatus includes a housing 50 having in its upper front portion a lid 51 pivoted at its upper horizontal edge to the housing 50. A generally pot-shaped receptacle 52 with a reflective inner surface is disposed within a vacuum-tight chamber 53 located in the housing 50 and is accessible from outside the housing when the lid 51 is open. The chamber 53 includes a total of four openings, one being closed by the lid 51 and sealed by a sealing 54 whereas a second and a third opening are sealed by glass plates 55, 55' of highly radiation-transmissive and heat-resistant quartz glass, and sealings 56, 56'. A fitting 57 is inserted into the fourth opening and is connected to a vacuum pump (not shown) preferably located inside the housing 50. The fitting has a valve 58 for venting the sealed chamber 53 when the vacuum pump is shut off.

A glass support 59 for holding dentals objects to be irradiated is disposed in a central aperture in the bottom of the receptacle 52. The support 59 is made of highly radiation-permeable glass.

A lamp 11 with a surrounding reflector 12 principally similar to the lamp and reflector used in the embodiments of FIGS. 2, 4 and 5 is mounted in the housing 50 in such a manner that the useful radiation emitted by the lamp 11 is reflected by the reflector 12 horizontally, the radiation being re-directed by a mirror 60 mounted on the inner side of the lid 51 so as to extend at an angle of 45° with respect to the reflector 12 and the receptacle 52. The thus redirected radiation is incident on the dental object placed on the support 59 in a vertical direction from above.

A second lamp 11' surrounded by a second reflector 12' is disposed underneath the support 59, this arrangement being again similar to the lamp and reflector used in the embodiments of FIGS. 2, 4 and 5, and the useful radiation of the desired spectral range is reflected by the reflector 12' vertically upwardly and is incident on the radiation object from the lower side thereof through the glass support 59. A filter 35 similar to the filter 35 in the embodiments of FIGS. 2, 4 and 5 is disposed between the lamp 11 and the glass plate 55, and another filter 35' of this type is disposed between the lamp 11' and the glass plate 55'. The filters 35 and 35' are mounted so as to be exposed to cooling air drawn by the blower 16 through air inlet openings provided in the lower part of the front wall of the housing 50.

Each reflector 12, 12' is surrounded by a metal shielding funnel 61, 61' which prevents the radiation transmitted by the reflector 12, 12', which is predominantly heat radiation, from impinging on the inner surfaces of the housing 50. Each lamp 11, 11' is mounted in a socket 18, 18' and may be removed therewith through corresponding access openings provided in the housing 50. More specifically, access to the lamp 11 is obtained by opening the rear wall of the housing 50, whereas access to the lamp 11' is obtained through an opening in the bottom wall provided with a closure 62.

Figure 7:
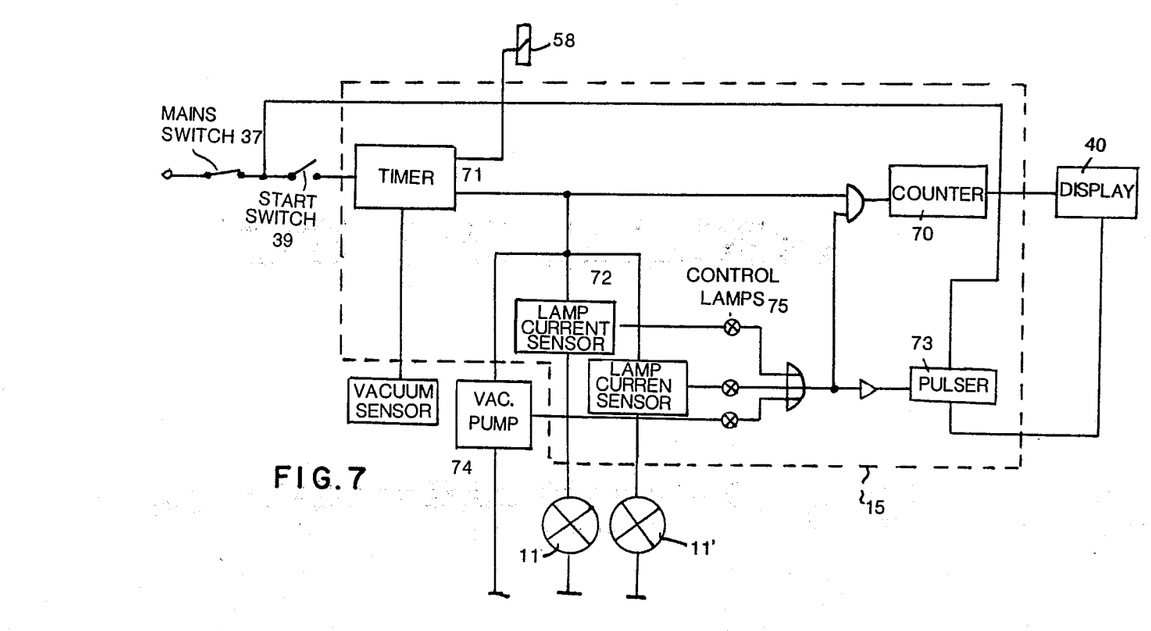
FIG. 7 is an electrical schematic diagram of the apparatus of the present invention.

In operation of the apparatus shown in FIG. 6, and with further reference to FIG. 7, the lid 51 will be opened and the irradiation object is placed on the support 59. Upon closing the lid 51, the operator will actuate a start switch 39, which is not shown but similarly as in FIG. 1 provided on the front side of the housing 50, thereby causing the control circuit 15 to actuate the vacuum pump 74 and, when a predetermined vacuum has been reached, to switch on the lamps 11, 11'. When the lamps are switched on, a counter 70 is started which drives a digital display (similar to the display 40 shown in FIG. 1). Upon expiry of the predetermined period of time, the control circuit 15 will switch off the lamps 11 and 11' and the vacuum pump 74 and vent the chamber 53 so that the lid 51 may be re-opened and the finished object removed. Control lamps 75 of FIG. 7 are provided on the front side of the housing to indicate the proper operation of the vacuum pump and each lamp. In case of malfunction of either lamp or of the vacuum pump, the control circuit 15 will stop the counter and provide the digital display with a flashing signal.

In the embodiment shown in FIG. 6, the support 59 for the irradiation object is completely stationary. This is of advantage particularly in those cases in which delicate objects are to be treated. Easy access to the support is obtained through the obliquely extending lid 51 from above, which is possible due to the disposition of the (upper) reflector 12 and lamp 11. At the same time, the horizontal disposition of the lamp 11 in FIG. 6 is preferred over the suspended disposition of the lamp in FIGS. 2, 4 and 5, because there is no danger of excessive heating of the lamp socket 18.

We claim:

1. An apparatus for treating dental objects with radiation of a selected spectral range, comprising
   (a) a housing,
   (b) support means including a horizontal glass plate for holding an object and being transparent for radiation of said selected spectral range,
   (c) a first lamp for emitting radiation containing said selected spectral range,
   (d) a first reflector for reflecting radiation of said selected spectral range, said first lamp and reflector being disposed so as to direct radiation in a substantially transverse direction,
   (e) a mirror disposed above said support means to redirect the radiation from said first lamp and reflector to said support means, said mirror being removable to allow access to said support means,
   (f) a second lamp disposed below said support means and emitting radiation containing said selected spectral range, and
   (g) a second reflector disposed below said support means and reflecting radiation of said selected spectral range substantially upwardly through said glass plate.

2. The apparatus of claim 1, wherein said selected spectral range is between about 400 nm and about 500 nm, at least one of said first and second reflectors being transparent for radiation above said selected spectral range.

3. The apparatus of claim 1, wherein said first and second reflectors are substantially paraboloid-shaped.

4. The apparatus of claim 1, wherein said first and second reflectors are disposed so as to surround said first and second lamps, respectively, and are transparent for radiation above said selected spectral range.

5. The apparatus of claim 1, wherein said support means is enclosed in a vacuum tight chamber, said chamber including means for connection to a vacuum source, first and second transparent windows opposing said first and second lamps and reflectors, respectively, a lid carrying said mirror, and means for sealing said lid when in its closed position.

6. The apparatus of claim 5, comprising first and second filter means for transmitting radiation of said selected spectral range and adsorbing radiation above said selected spectral range, said filter means being disposed between said windows and said first and second lamps and reflectors, respectively.

7. The apparatus of claim 6, comprising means for drawing cooling air along said first and second filter means.

8. The apparatus of claim 1, comprising a control circuit for switching off said lamps upon expiry of a predetermined time interval after the lamps have been switched on.

9. The apparatus of claim 8, comprising a counter and a visual count display, said control circuit including means for indexing said counter during said time interval, and means for stopping said counter and intermittently actuating said display upon interruption of current supplied to at least one of said lamps.

10. The apparatus of claim 5, comprising a visual display and means for intermittently actuating said display upon malfunction of said vacuum source.

* * * * *